United States Patent [19]

Tanaka

[11] Patent Number: 5,425,942
[45] Date of Patent: Jun. 20, 1995

[54] POLYFUNCTINAL PROTEASE

[75] Inventor: Keiji Tanaka, Tokushima, Japan

[73] Assignee: Otsuka Pharamceutical Co., Ltd., Tokyo, Japan

[21] Appl. No.: 27,595

[22] Filed: Mar. 5, 1993

Related U.S. Application Data

[62] Division of Ser. No. 783,935, Oct. 29, 1991, abandoned, which is a division of Ser. No. 363,007, Jun. 8, 1989, abandoned.

[30] Foreign Application Priority Data

Jun. 8, 1988 [JP] Japan .................. 63-142526

[51] Int. Cl.$^6$ .................. C12N 9/00; C12N 9/48; C12N 9/58
[52] U.S. Cl. .................. 424/94.1; 424/94.63; 424/94.64; 435/212; 435/219; 435/224; 435/183; 435/940; 435/942
[58] Field of Search .................. 424/94.1, 94.63, 94.64; 435/212, 219, 224, 183, 940, 942

[56] References Cited

FOREIGN PATENT DOCUMENTS 2233038 1/1975 France .
1255284 12/1971 United Kingdom .

OTHER PUBLICATIONS

Chemical Abstract, vol. 108, 1988, p. 437, Abstract No. 3564k, Columbus, Ohio, US; S. Beck et al.: "Production of lipolytic and proteolytic factors by an murine tumor-producing cachexia in the host".

Biological Abstracts, vol. 78, No. 1, 1984, Abstract No. 4750, Phila. PA, US; F. C. Lowe et al.: "Biochemical methods for predicting metstatic ability of prostatic cancer utilizing the Dunning R-3327 rat prostatic adenocarcinoma system as a model".

Biotec., vol. 1, 1987, pp. 119-130, Stuttgart, DE; M. Bahn et al.: "Enzymes for detergents", pp. 119-128.

S. Ferrone et al.: "Handbook of Monoclonal Antibodies", 1985, pp. 131-149, Noyes Publications, Park Ridge, US; Chapter 9: F. Celada et al.: "Monocional antibodies in enzymology".

Cell Structure and Function, vol. 12, No. 6, 1987, p. 601 "A high molecular weight multi-protease complex distributed ubiquitously in a variety of eukaryotic cells".

The Journal of Biological Chemistry, vol. 263, No. 31, No. 5, 1988, pp. 16209-16217 "Proteasomes as 20S ring shaped particles in a variety of eukaryotic cells".

Arrigo, et al. Nature vol. 331 14 Jan. 1988.

Tanaka, et al. J Biological Chemistry vol. 261 No. 32 pp. 15197-15203 1986.

*Primary Examiner*—William H. Beisner
*Assistant Examiner*—Jane A. Williams
*Attorney, Agent, or Firm*—Sughrue, Mion, Zinn, Macpeak & Seas

[57] ABSTRACT

The present invention provides a human polyfuctional protease chracterized in that the protease has unique enzymological and physicochemical properties:

1 Claim, 9 Drawing Sheets

FIG. 7
Top--
Bottom--

POLYFUNCTINAL PROTEASE

This is a divisional of application Ser. No. 07/783,935 filed Oct. 29, 1991, now abandoned, which is a divisional application of Ser. No. 07/363,007 filed Jun. 8, 1989, now abandoned.

BACKGROUND OF THE INVENTION

The present invention relates to polyfunctional proteases, and more particularly to polyfunctional proteases as novel intracellular proteases.

The polyfunctional protease, which is locally present in the cytoplasm as an inactive protease, was separated from the rat livers by the present inventor and its functions, molecular structure, distribution, locality, etc were reported (The Journal of Biological Chemistry, 261(32), pp 15197–15203; 1986 ibid. pp 15204–152-7 (1986); Kagaku to Seibutsu 25(8), pp 489–490 (1987); Tanpakushitsu Kakusan Kouso 32(7), pp 955–961 (1987); etc. ).

The above protease is believed to have a molecular weight of about 750,000, which is exceptionally large for a protease. The protease is a giant protein complex in the form of heteropolymer and has in one molecule a plurality of catalytic sites which are different in substrate specificity and independent of one another. For this reason the protease is referred to as a "polyfunctional protease". When observed through a electron microscope, the molecule of this enzyme is found to be of an annular particle structure. Therefore, the protease is also referred to as "proteasome"(Nature, 331, 192–194 (1988) This protease is believed to be an enzyme in a non-lysosomal proteolytic pathway.

SUMMARY OF THE INVENTION

An object of the present invention is to provide novel polyfunctional proteases, i.e., human, chicken, *Xenopus laevis* and yeast (*S. cerevisiae*) polyfunctional proteases (hereinafter referred to as "proteasomes").

Another object of the invention is to provide anti-proteasome antibodies useful for purifying and determining the respective proteasomes and antigens for preparing the antibodies.

Still another object of thereto invention is to provide methods of immunologically purifying or determining the proteasome with use of the antibody, and techniques for screening and/or diagnosing cancers by determining the proteasome in the body fluid.

The present invention provides a human proteasome characterized by the following enzymological and physicochemical properties.

a. Enzymatic activity capable of cleaving the synthetic substrate Cbz-Leu-Leu-Glu-NA (wherein Cbz represents N-benzyloxycarbonyl, and NA represents 2-naphthylamido, the same hereinafter), and an optimum pH of 8.4 to 8.6.

b. Enzymatic activity capable of cleaving the synthetic substrate Cbz-Ala-Arg-Arg-MNA (wherein MNA represents 4-methoxy-2-naphthylamido, the same hereinafter), and an optimum pH of 9.8 to 10.1.

c. Emzymatic activity capable of cleaving the synthetic substrate of Suc-Leu-Leu-Val-Tyr-MCA (wherein Suc represents succinyl, and MCA represents 4-methyl-7-cumarylamido, the same hereinafter), and an optimum pH of 8.4 to 8.6.

d. An ultraviolet absorption spectrum with a maximun absorption ($\lambda$max) at 278 nm and an absorption of $E_{1\ cm}^{1\%}=11.2$ at 280 nm.

e. A sedimentation constant ($S_{20,W}$) of 21.8 S as determined by the sedimentation velocity method.

f. A diffusion coefficient ($D_{20,W}$) of $2.28 \times 10^{-7}$ cm$^2$.S$^{-1}$ as determined by the quasi-elastic light scattering method.

g. A molecular weight of $870000 \pm 50000$.

h. An isoelectric point (pI) of $5.0 \pm 0.2$ as determined by isoelectric focusing.

i. The following amino acid composition (mole %):

| Asx | 8.4 | Phe | 3.4 |
|---|---|---|---|
| Glx | 12.4 | Tyr | 4.6 |
| Arg | 5.5 | Trp | 0.3 |
| Lys | 6.2 | Ser | 5.8 |
| His | 1.9 | Thr | 5.4 |
| Ala | 9.5 | ½Cys | ND |
| Gly | 8.1 | Met | 3.1 |
| Leu | 8.8 | Pro | 3.6 |
| Ile | 5.7 | Val | 7.2 | wherein ND means that the amino acid is not detectable, the same as hereinafter.

The symbols representing the component amino acids of the amino acid composition used herein are in accordance with the nomenclature adopted by IUPAC-IUB or those conventional in the art. These symbols represent the following.

| Asx: aspartic acid and asparagine | Tyr: tyrosine |
|---|---|
| Glx: glutamic acid and glutamine | Trp: tryptophan |
| Phe: phenylalaine | Ser: serine |
| Arg: arginine | Thr: threonine |
| Lys: lysine | ½Cys: cysteine |
| His: histidine | Met: methionine |
| Ala: alanine | Pro: proline |
| Gly: glycine | Val: valine |
| Leu: leucine | |
| Ile: isoleucine | |

The absorption value of the ultraviolet absorption spectrum, the sedimentation constant given by the sedimentation velocity method, the diffusion coefficient determined by the quasi-elastic light scattering method, the amino acid contents (mole %) and other measurements obtained by physical methods herein given are all experimental values with a standard deviation of up to 5%.

The present invention further provides a chicken polyfuctional protease characterized by the following enzymological and physicochemical properties.

a. Enzymatic activity capable of cleaving the synthetic substrate Cbz-Leu-Leu-Glu-NA, and an optimum pH of 8.4 to 8.7.

b. Enzymatic activity capable of cleaving the synthetic substrate Cbz-Ala-Arg-Arg-MNA, and an optimum pH of 9.6 to 10.1.

Enzymatic activity capable of cleaving the synthetic substrate Suc-Leu-Leu-Val-Tyr-MCA, and an optimum pH of 8.0 to 8.5.

d. An ultraviolet absorption spectrum with a maximum absorption ($\lambda$max) at 278 nm and an absorption of $E_{1\ cm}^{1\%}=10.8$ at 280 nm.

e. A sedimentation constant ($S_{20,W}$) of 20.0 S as determined by the sedimentation velocity method.

f. A diffusion coefficient ($D_{20,W}$) of $2.02 \times 10^{-7}$ cm$^2$. S$^{-1}$ as determined by the quasi-elastic light scattering method.

g. A molecular weight of $910000 \pm 50000$.

h. An isoelectric point (pI) of $4.9 \pm 0.2$ as determined by isoelectric focusing.

i. The following amino acid composition (mole %):

| Asx | 8.2 | Phe | 3.3 |
|---|---|---|---|
| Glx | 13.1 | Tyr | 4.5 |
| Arg | 5.4 | Trp | 0.4 |
| Lys | 6.0 | Ser | 6.1 |
| His | 1.9 | Thr | 5.5 |
| Ala | 9.4 | ½Cys | ND |
| Gly | 8.5 | Met | 2.8 |
| Leu | 8.3 | Pro | 3.6 |
| Ile | 5.7 | Val | 7.0 |

The present invention further provides a Xenopus polyfuctional protease characterized by the following enzymological and physicochemical properties.

a. Enzymatic activity capable of cleaving the synthetic substrate Cbz-Leu-Leu-Glu-NA, and an optimum pH of 8.9 to 9.2.

b. Enzymatic activity capable of cleaving the synthetic substrate Cbz-Ala-Arg-Arg-MNA, and an optimum pH of 9.6 to 10.5.

c. Enzymatic activity capable of cleaving the synthetic substrate Suc-Leu-Leu-Val-Tyr-MCA, and an optimum pH of 8.4 to 8.8.

d. An ultraviolet absorption spectrum with a maximum absorption ($\lambda$max) at 278 nm and an absorption of $E_{1\ cm}^{1\%} = 12.3$ at 280 nm.

e. A sedimentation constant ($S_{20,W}$) of 19.6 S as determined by the sedimentation velocity method.

f. A diffusion coefficient ($D_{20,W}$) of $2.15 \times 10^{-7}$ cm$^2$. S$^{-1}$ as determined by the quasi-elastic light scattering method.

g. A molecular weight of $840000 \pm 50000$.

h. An isoelectric point (pI) of $5.0 \pm 0.2$ as determined by isoelectric focusing.

i. The following amino acid composition (mole %):

| Asx | 8.7 | Phe | 3.4 |
|---|---|---|---|
| Glx | 12.5 | Tyr | 4.9 |
| Arg | 5.2 | Trp | 0.3 |
| Lys | 6.7 | Ser | 5.7 |
| His | 1.8 | Thr | 5.5 |
| Ala | 9.5 | ½Cys | ND |
| Gly | 7.9 | Met | 3.0 |
| Leu | 8.7 | Pro | 3.3 |
| Ile | 5.8 | Val | 7.1 |

The present invention further provides a yeast polyfuctional protease characterized by the following enzymological and physicochemical properties.

a. Enzymatic activity capable of cleaving the synthetic substrate Cbz-Leu-Leu-Glu-NA, and an optimum pH of 8.4 to 8.8.

b. Enzymatic activity capable of cleaving the synthetic substrate Cbz-Ala-Arg-Arg-MNA, and an optimum pH of 9.6 to 10.0.

c. Enzymatic activity capable of cleaving the synthetic substrate Suc-Leu-Leu-Val-Tyr-MCA, and an optimum pH of 8.4 to 8.7.

d. An ultraviolet absorption spectrum with a maximum absorption (max) at 278 nm and an absorption of $E_{1\ cm}^{1\%} = 7.4$ at 280 nm.

e. A sedimentation constant ($S_{20,W}$) of 20.0 S as determined by the sedimentation velocity method.

f. A diffusion coefficient ($D_{20,W}$) of $2.60 \times 10^{-7}$ cm$^2$. S$^{-1}$ as determined by the quasi-elastic light scattering method.

g. A molecular weight of $710000 \pm 50000$.

h. An isoelectric point (pI) of $4.6 \pm 0.2$ as determined by isoelectric focusing.

i. The following amino acid composition (mole %):

| Asx | 11.0 | Phe | 2.8 |
|---|---|---|---|
| Glx | 12.9 | Tyr | 3.5 |
| Arg | 3.6 | Trp | 0.4 |
| Lys | 6.2 | Ser | 6.2 |
| His | 1.3 | Thr | 5.5 |
| Ala | 8.9 | ½ Cys | ND |
| Gly | 9.4 | Met | 1.8 |
| Leu | 8.3 | Pro | 4.5 |
| Ile | 6.5 | Val | 7.1 |

The present invention further provides antibodies characterized in that they are specifically reactive with the respective proteasomes only individually, i.e., an anti-human proteasome antibody, anti-chicken proteasome antibody, anti-*Xenopus laevis* proteasome antibody and anti-yeast proteasome antibody.

DETAILED DESCRIPTION OF THE INVENTION

The proteasome of the present invention is a complex of proteases which differs in substrate specificity, and has the ability to cleave proteins at any of acid, neutral and basic sites and can therefore be said to be the most powerful protease in the history of research on proteases. Moreover, the expression of its activity is controlled intramolecularly, and the proteasome is activated by the plasmin in the blood and is therefore useful as a fibrinolytic agent. The proteasome of the present invention is usable also as an additive for detergents and cosmetics.

The anti-proteasome antibody provided by the present invention and specific to the proteasome is useful for purifying and assaying the proteasome. The proteasome can be immunologically purified and assayed by the antibody. Furthermore, cancers can be screened and/or diagnosed by determining the proteasome in the body fluid with the antibody.

The proteasomes of the invention can be prepared by the processes described below in detail.

The proteasome of the present invention can be obtained from a cytoplasmic fraction of the animal or microorganism from which it is to be derived, by usual purification and isolation methods. The proteasome is widely distributed in various cells and tissues, and the origin cell is not limited specifically. In humans, the proteasome content is high in organs having high metabolic activity, especially in the liver. Accordingly it is desirable to use cells of such organs as the origin. Further the cells to be used may be derived from various established cell lines.

Preparation of the cytoplasm fraction from origin cells is known and can be accomplished by the usual cell fractionation method. For example, the cytoplasm fraction is preferably a supernatant obtained by centrifuging a homogenate of origin cells to remove the cell fraction including the cell membrane, nucleus, mitochondrion, lysosome and microsome.

The present proteasome can be isolated from the cytoplasm fraction and purified by various procedures utilizing the physicochemical and immunochemical properties of the proteasome (see, for example, "Biochemical Data Book II," pp. 1175–1259, first edition, first print, Jun. 23, 1980, published by Tokyo Kagaku Dojin Co., Ltd.). More specifically, useful methods include, for example, treatment with a protein precipitating agent, ultrafiltration, molecular sieve chromatography (gel filtration), adsorption chromatography involving ion exchange, partition chromatography and like liquid chromatographic methods, centrifuging, electrophoresis, dialysis and combinations of such methods.

The present proteasome is present in an inactive form within the cells and in the extracted fraction, but is irreversibly activated during purification. The enzyme is very unstable and difficult to isolate and purify when activated, and must therefore be maintained in the inactive form at all times. The enzyme can be maintained in the inactive form, for example, by incorporating in the separation solvent of 20% glycerol and 10 mM 2-mercapto ethanol or 1 mM dithiothreitol.

The proteasome of the present invention obtained as a homogeneous substance by the isolation and purification procedure, is identified by the foregoing enzymological and physicochemical properties.

The present proteasome thus obtained can be used as an immunogen for preparing an antibody (anti-proteasome antibody) which is specifically reactive with the proteasome.

The anti-proteasome antibody is identified as an antibody which specifically recognizes only the type of proteasome of the same origin and is characterized in that the proteasome is not cross-reactive with proteasomes derived from other origins. This antibody can be prepared, for example, from the proteasome of the invention serving as an immunogen. When the antibody is a polyclonal antibody, the proteasome to be used as the immunogen needs to be as homogeneous as the present proteasome, whereas if the antibody is a monoclonal antibody, the homogeneous proteasome of the invention need not always be used but other immunogens containing the proteasome can be used.

The antibody can be prepared from the proteasome as the immunogen by usual methods, for example, by administering the immunogen to a mammal for immunization to produce the desired antibody (polyclonal antibody) the in vivo and collecting the antibody, or by fusing the plasmacyte (immunized cell) of the immunized mammal with a plasmacytoma cell compatible therewith to prepare a hybridoma, selecting a clone producing the desired antibody (monoclonal antibody) therefrom and incubating the clone.

Although the mammal to be immunized is not limited specifically, it is desirable to select a suitable animal in view of the compatibility of the plasmacyte with the plasmacytoma to be used for cell fusion in the case where the antibody specific to the proteasome of the invention is to be prepared with use of hybridoma. Generally, a mouse, rat or the like is advantageous to use. The mammal can be immunized by usual methods, for example, by giving the immunogen intraveneously, intracutaneously, subcutaneously, intraperitoneally or otherwise. More specifically, the immunogen is given several times (booster), in combination with a usual adjuvant at a overall dose of about 200 to about 250 μg/body in the case of a mouse.

The polyclonal antibody can be collected by separating off the serum of the immunized mammal one to two weeks after the final administration.

Suitable immunized cells for use in preparing the monoclonal antibody include the spleen cell removed from the mammal about three days after the final administration. Examples of immunized cells for use as parent cells to be fused with such immunized cells are those derived from known established cell lines, e.g. myeloma cells such as P3 (p3/X63-Ag8) [Nature, 256, 495–497 (1975)], P3-U1 [Current Topics in Microbiology and Immunology, 81, 1–7 (1978)], NS-1 [Eur. J. Immunol., 6, 511–519 (1976)], MPC-11 [Cell, 405–415 (1976)], SP2/0 [Nature, 276, 269–270 (1978)], FO [J. Immunol. Meth., 35, 1–21 (1980)], X63.6.5.3 (J. Immunol., 123, 1548–1550 (1979)], S194 [J. Exp. Med., 148, 313–323 (1978)], R210 [Nature, 277, 131–133 (1979)].

Methods of preparing monoclonal antibodies from hybridomas are known; for example, the method of Milstein et al. can be used to (Method in Enzymology, Vol. 73, p.3, (1981)). The fusion reaction can be conducted by a suitable method, such as a method wherein polyethylene glycol (PEG), hemagglutinating virus of Japan (HVJ) or the like is used, or an electrical fusion method. The hydridoma method is not the only method possible; also usable is a method wherein the immunized cell is immortalized using Epstein-Barr virus.

The hybridoma or immortalized cells thus obtained are monocloned by the usual limiting dilution method to select the desired antibody producing clone.

The desired antibody producing clone can be selected by various methods generally used for detecting antibodies, for example, by the ElISA method (Meth. Enzymol., 70, 419–439 (1980)), plaque method, spot method, agglutination method and radioimmunoassay (RIA) ("Hybridoma Methods and Monoclonal Antibodies," published by R & D Planning Co., Ltd., pp. 30–53, Mar. 5, 1982). The immunogen can be utilized for screening procedures.

The resulting cells producing the monoclonal antibody can be subcultured with a usual medium and preserved for a prolonged period of time in liquid nitrogen.

The antibody can be collected from the clone by incubating the clone in a usual manner and preparing a supernatant from the culture, or by administering the clone to a mammal compatible therewith for proliferation and collecting the ascitic fluid from the mammal. The former method is suitable for preparing the antibody with a high purity, while the latter method is suited to quantity production.

The antibody thus obtained can be purified by usual methods such as salting out, gel filtration or affinity chromatography.

With use of the antibody, it is possible to purify the proteasome by an immunological method such as affinity chromatography.

It is also possible to determine the protease by various immunological methods using the antibody.

Our research has revealed that large quantities of proteasome are present in body fluids of cancer patients, and that the amount is so distinguishable from the corresponding amount in the normal person as to be diagnostically significant. Accordingly, the proteasome determining technique is very useful for screening and/or diagnosing cancers.

The determination of the proteasome in the body fluid for screening and/or diagnosing cancers can be accomplished basically by usual methods of immunoassays such as RIA and enzymatic immunoassay. Procedures for practicing these methods include the competitive method, sandwich method, agglutination method, etc.

Examples of body fluids to be assayed are blood, tissue fluid, lympth, pleural fluid, ascites fluid, amniotic fluid, gastric juice, urine, pancreatic juice, cerebrospinal fluid, saliva and the like. Among these blood, especially serum and plasma are especially desirable.

Cancers can be screened or diagnosed advantageously by comparing the proteasome level of the subject thus determined with the corresponding level of a normal person.

Cancers can be screened or diagnosed conveniently using a kit for determining the proteasome in the body fluid. The kit comprises an antibody reagent consisting essentially of the anti-proteasome antibody. A stabilizer such as glycerol, bovine or like serum protein and/or a preservative can be admixed with the reagent. Although the buffer is not an essential component of the kit, various buffers can be added to the reagent for use in the determination for adjusting the reagent to a pH of about 4 to 8.

EXAMPLES

The present invention will be described in more detail with reference to the following examples, but is not limited by these examples.

The protease activity was determined using [$^3$H]methyl-casein according to the method of Tanaka et al. (J. B. C., 261(32), pp 15197–15203 (1986)). The protease activity can be easily and more sensitively determined by evaluating the lytic activity of a fluorescent peptide substrate such as Suc-Leu-Leu-Val-Tyr-MCA. The process for preparing the proteasome was practiced at a temperature of not more than 4° C. using as buffer 50 mM Tris HCl buffer (pH 7.5) containing 1 mM dithiothreitol and 20% glycerol unless otherwise specified.

EXAMPLE 1

Preparation of Human Proteasome

A 200 g quantity of human liver tissue was homogenized with a buffer (50 mM Tris HCl buffer, pH 7.5, containing 0.1 mM EDTA, 1 mM dithiothreitol and 0.25M sucrose) in 3 times the volume of the tissue using a homogenizer (Potter. Elvehjem homogenizer), and centrifuged (105000×g, 60 mins), giving a cytoplasm fraction as supernatant.

The liver supernatant fraction obtained above was admixed with 800 ml of Fast Flow Q-Sepharose (product of Pharmacia Fine Chemicals) equilibrated with the buffer, and the mixture was stirred by a magnetic stirrer at 4° C. for 1 hour. The resulting resin was transferred into a Buechner funnel, washed and applied to a column (5 cm in diameter, 60 cm in length). Subsequently the column was washed with the buffer until the washing had a absorbance reduced to below 0.2. The specimen adsorbed on the column was eluted with a linear gradient of 0 to 0.8M NaCl (2 l, 10 ml of fraction). The protease activity was recovered in the fraction at about 0.4M NaCl.

The active fraction obtained was precipitated with polyethylene glycol 6000 (terminal concentration: 15%) and the precipitate was dissolved in a small amount (20 ml) of the buffer. The solution was applied to a Biogel A-1.5 m column (product of Japan Bio Rad Laboratories, Co., Ltd., 4 cm in diameter, 80 cm in length) and eluted with the buffer (the flow rate was 26 ml/min, and the eluate was collected in 10 ml of fraction). The active fraction of a single peak was collected.

Subsequently the fraction obtained was dialyzed against 10 mM potassium phosphate buffer (pH 6.8) containing 1 mM of dithiothreitol and 20% glycerol, applied to a 40 ml column of Hydroxy Apatite (product of Japan Bio Rad Laboratories, Co., Ltd.) equilibrated with the same buffer. The column was then washed with the same buffer, and the specimen adsorbed on the column was eluted with a linear gradient of 10 to 300 mM phosphate (400 ml, 4 ml fraction). The activity was recovered in the fraction at about 220 mM phosphate.

The active fraction was applied to a 20 ml column of Heparin-Sepharose CL-6B (product of Pharmacia LKB Biotechnology Inc.) equilibrated with the buffer. The column was washed with the buffer to the base line absorbance, followed by elution with a linear gradient from 0 to 0.4M KCl (400 ml, 4 ml fraction). The activity was recovered in the fraction at about 100 mM KCl.

The active fraction obtained above was applied to Mono-Q Column (product of Pharmacia LKB Biotechnology Inc., 1 cm in diameter and 10 cm in length) equilibrated with 25 mM Tris HCl buffer (pH 7.5) containing 1 mM dithiothreitol and 20% glycerol and eluted by high-performance liquid chromatography (FPLC-System, product of Pharmacia LKB Biotechnology Inc.) with a linear gradient from 0 to 0.8M KCl (the flow rate was 1 ml/mim).

The desired homogeneous human proteasome was thus recovered in the fraction at about 340 mM KCl.

EXAMPLE 2

Preparation of Chicken Proteasome, Xenopus Proteasome and Yeast Proteasome

The desired proteasome was prepared from chicken liver tissues in the same manner as in Example 1.

By continuous chromatography (Tanaka et al., ibid.), the xenopus proteasome and the yeast proteasome were obtained from the ovary of *Xenopus laevis* and *S. cerevisiae*, respectively.

EXAMPLE 3

(1) Preparation of Anti-Proteasome Antibody

According to the method of Winberry and Holter (J. Biol. Chem., 252, 7796–7801 (1977)), the antibodies (polyclonal antibodies) against each of the proteasomes obtained in Examples 1 and 2 were prepared as follows.

A 5 mg quantity of each of the above proteasomes was emulsified in a specified amount of a complete Freund's adjuvant (manufactured by Difco). The emulsion was administered pareterally to the foot-pad and back of female white rabbits weighing 2.5 kg. Four weeks later, one-half of the above injected dose was given as a booster dose. One more week later, a booster dose of the emulsion was administered again to immunize the test animal.

Blood was collected from the animal immunized and serum was isolated. IgG fraction was separated from the serum by protein A-Sepharose affinity chromatography (FEBS Lett., 28, 73–76 (1972)) to obtain the antibody against the proteasome.

(2) Preparation of Monoclonal Antibody

The monoclonal antibody against the proteasome of the present invention obtained above was prepared as follows.

A 500 μl quantity of a phosphate buffer saline (PBS, pH 7.4) containing 100 μg of the proteasome was admixed with the same equal amount of a Freund's adjuvant. The dispersion obtained was subcutaneously administered to BALB/c mouse at a dose of 20 μg of the proteasome. In the second week, the same dispersion was similarly administered. Two more weeks later, 200 μg of the purified proteasome in physiological saline was subcutaneously administered. Three days after this final administration, the spleen was removed from the test animal, and spleen cells were washed three times with RPMI-1640 medium.

In addition, the mouse myeloma cell line P3U1 (Current Topics in Microbiology and Immunology, 81, 1–7 (1978)) was washed in the same manner as above, and then the myeloma cells ($4 \times 10^7$ cells) were admixed with the above spleen cells ($2 \times 10^8$ cells) in a 500 ml-centrifuge tube. After centrifugation at 200 G for 5 minutes, the supernatant was removed using a Pasteur pipette. To the pellets obtained was added dropwise over a period of one minute 2 ml of RPMI-1640 medium maintained at 37° C. and containing 50% (w/v) polyethylene glycol 1500 (manufactured by Boehringer Mannheim Yamanouchi). Thereto was added 1 ml of RPMI-1640 medium (maintained at 37° C.) free from fetal calf serum (FCS), and the mixture was left to stand for one minute. A 2 ml quantity of the same FCS-free medium was further added, and the resulting mixture was left to stand for 2 minutes. Subsequently thereto was added 8 ml of RPMI-1640 medium (37° C.) containing 15% FCS, 0.05 g/l streptomycin, 60000 U/l potassium penicillin G, 54 mg/l gentamycin and 1 mM pyruvate (hereinafter referred to as "complete RPMI medium"), and the mixture was centrifuged at 200 g for 5 minutes. The pellets separated from the supernatant were dispersed in the complete RPMI medium maintained at 37° C. in an amount of $2 \times 10^6$ spleen cells/ml. A 1 ml quantity of the dispersion was placed into each of 24 wells of a microplate (manufactured by Costar Corporation) and incubated at 37° C. in an incubator in the presence of 5% $CO_2$ gas. After 24 hours, 1 ml of the complete RPMI medium containing $1.0 \times 10^{-4}$M hypoxanthine, $4.0 \times 10^{-7}$ aminopterin and $1.6 \times 10^{-5}$M thymidine (hereinafter referred to as "HAT medium") was placed into the well. On 3rd, 5th and 7th days one-half of the supernatant was replaced by the fresh HAT medium and on 9th day one-half of the supernatant was replaced by the complete RPMI medium containing $1.0 \times 10^{-4}$M hypoxanthine and $1.6 \times 10^{-5}$M thymidine (hereinafter referred to as "HT medium"). Similarly on 12th, 15th, 18th and 21st days one-half of the supernatant was replaced by the HT medium and on 24th day one-half of the supernatant was replaced by the complete RPMI medium. The cell growth was thereafter maintained using this complete RPMI medium.

The hybridomas thus obtained were cloned by limiting dilution. More specifically, the culture was diluted so that $2.5 \times 10$ cells/ml of the hybridoma and $4 \times 10^8$ BALB/c mouse thymus cells/ml were contained in complete RPMI medium. The dilution was placed into 96 wells of a microplate so that 5 hybridomas were present in each well, followed by incubation. The grown hybridomas were further diluted to 0.5 hybridoma/well in the same manner as above, and cloning was done.

Screening for the clone producing the desired antibody was conducted. More specifically, 50 μl of the supernatant of the cloning culture was placed into each of 96 wells of a microplate wherein the purified proteasome and bovine serum albumin (BSA) were insolubilized, to effect reaction with stirring at room temperature for one hour. After the reaction, the unreacted substances were removed by washing with distilled water. A 100 μl portion of 6000-fold dilution of anti-mouse IgG (product of Cappel) labeled with peroxidase was placed into each well, and allowed to react with stirring at room temperature for 30 minutes. Then the unreacted substances were withdrawn by washing with distilled water. A 100 μl portion of a solution of o-phenylene diamine (2.5 mg/ml) in 0.015% aqueous $H_2O_2$ was placed into each well and allowed to stand at room temperature for 15 minutes. Thereto 100 μl of 2N $H_2SO_4$ solution was added to stop the reaction. The color-developed microplate was determined at 492 nm using a microreader (Titertek Multiskan MMC, Flow Labs., USA).

The above method afforded the desired antibody-producing clones, each specific only for a particular proteasome.

One of the antibody-producing clones derived from the human proteasome and specific for the human proteasome were deposited under the name of OAL HMWP-1 with deposition No. FERM P-9838 in Fermentation Research Institute, Agency of Industrial Science & Technology.

The clone No. OAL HMWP-1 was incubated in a complete RPMI medium at 37° C. for 48 hours in an incubator in the presence of 5% $CO_2$ gas. The culture was centrifuged at 3000 rpm for 10 minutes to separate a supernatant containing the desired monoclonal antibody.

(3) Identification of Class of Monoclonal Antibody

The monoclonal antibody obtained in (2) belongs to $IgG_1$ class, which was identified using Rat Monoclonal Typing Kit (product of Miles Scientific Laboratories Inc.).

(4) Purification of Monoclonal Antibody

In RPMI-1640, $1 \times 10^7$ cells of OAL HMWP-1 were dispersed. The dispersion was administered intraperitoneally to nude mice or nude rats. After 2 to 3 weeks the ascites fluid accumulated with a human proteasome antibody content of about 0.2 to 5 mg/m was recovered.

PBS was added to each of the culture supernatants obtained in (2) to prepare 2-fold dilution. The diluted supernatant was applied to a protein A column to prepare the anti-human proteasome antibody as purified.

(5) Preparation of Insolubilized Antibody

The purified anti-human proteasome antibody obtained in (4) was admixed with 50 mM PBS (pH 7.4) containing 0.15M NaCl and 0.05% $NaN_3$ to a protein concentration of 5 μg/ml.

Polyethylene beads (10000 beads, 4 mm in diameter, manufactured by Sekisui Kagaku Kogyo Co., Ltd.) were thoroughly washed with 0.001N aqueous solution of NaOH containing 30% ethanol. The beads were then washed with 0.001N aqueous solution of HCl and thoroughly washed with distilled water.

To 100 ml of the above antibody solution were added the above beads (800 beads). The mixture was stirred for 2 hours and left to stand overnight at 4° C. The beads were filtered off, washed with physiological saline, stirred for 2 hours in a solution of 50 mM PBS (pH 7.4) containing 0.5% crystalline BSA (manufactured by Seikagaku Kogyo Co., Ltd.) and then left to stand overnight at 4° C. The beads were filtered off to obtain an insolubilized antibody which was fully washed.

(6) Preparation of Labeled Antibody

A 100 μg quantity of the purified antibody obtained in (4) was dissolved in 0.1 ml of 0.1M borate buffer (pH 8.2), and thereto 1 mCi Na$^{125}$I (manufactured by NEN Research Products) was added. A solution of 2 ml/ml of Iodogen (product of Piece Chemical Company) in 20 μl of dichloromethane was placed into a glass tube, and the solvent was evaporated off in a stream of nitrogen gas to dry the tube. The above antibody solution was placed into this glass tube, and the mixture was allowed to stand for 5 minutes with ice-cooling. The reaction mixture obtained was transferred to another test tube and the reaction was concluded. Then the mixture was subjected to gel filtration (Sepharose CL-6B) and eluted with 50 mM phosphate buffer containing 0.15M NaCl, 0.1% BSA and 0.02% NaN$_3$ to collect IgG fraction corresponding to the radioactivity peak, giving $^{125}$I-labeled antibody. The reactivity of the human proteasome antibody was studied using the purified human proteasome.

The $^{125}$I-labeled antibody was also favourably prepared by the Chloramine T method (Nature, 194, 496 (1962)) and Bolton-Hunter method (Biochem. J., 89, 114 (1963)).

(7) Preparation of Peroxidase-labeled Antibody

A 10 mg quantity of the anti-human proteasome antibody obtained in (4) was dissolved in 1 ml of 0.1M phosphate buffer (pH 6.8), and the same buffer containing 10 mg/ml of peroxidase was added to the solution. The mixture was gently stirred and thereto 50 μl of 1% glutal aldehyde solution was added dropwise. The resulting mixture was allowed to react at room temperature for 2 hours and dialyzed against physiological saline all day long at 4° C., giving a peroxidase-labeled antibody.

Besides the above method, the periodate crosslink method (J. Histochem. Cytochem., 22, 1084-1091 (1974)), the maleimide crosslink method (J. Histochem. Cytochem., 78, 235-237 (1975)), the isocyanate crosslink method (J. Histochem. Cytochem., 21, 233-240 (1973)) and the benzoquinone crosslink method (Ann. Immunol., 127 c, 197-208 (1976)) provided desirable peroxidase-labeled antibodies.

Further, other enzymes such as β-G-galactosidase, alkaline phosphatase, malate dehydrogenase, glucose-6-phosphate dehydrogenase, glucose oxidase, acetylcholinesterase, glucoamyrase and lysozyme can be used instead of peroxidase to obtain the desired labeled antibody.

(8) Preparation of Fluorescence-labeled Antibody

A 10 mg quantity of the purified anti-human proteasome antibody obtained in (4) was dissolved in 1 ml of 0.05M carbonate buffer (pH 9.5) and the same buffer containing 100 μg/ml of FITC was added dropwise to the solution. The mixture was stirred at room temperature for one hour, and then dialyzed against 0.005M phosphate buffer all day long. The dialyzate was purified by means of ion-exchange using DEAE-Sepharose to give FITC-labeled human proteasome antibody.

Besides, by employing RITC (tetramethyl rhodamine isothiocyanate ), the desired RITC-labeled human proteasome antibody was similarly obtained.

The proteasomes of the present invention obtained in Examples 1 and 2 were tested for enzymatic activity, physiological properties, shape and immunological properties, and subjected to amino acid analysis, electrophoresis and chromatography.

BRIEF DESCRIPTION OF THE DRAWINGS

The results of these tests are shown in the accompanying drawings, in which:

FIGS. 7 and 8 show the electrophoresis patterns of proteasomes of the invention;

<CHARACTERISTICS OF PROTEASOME>

(i) Activity

Figure 1:
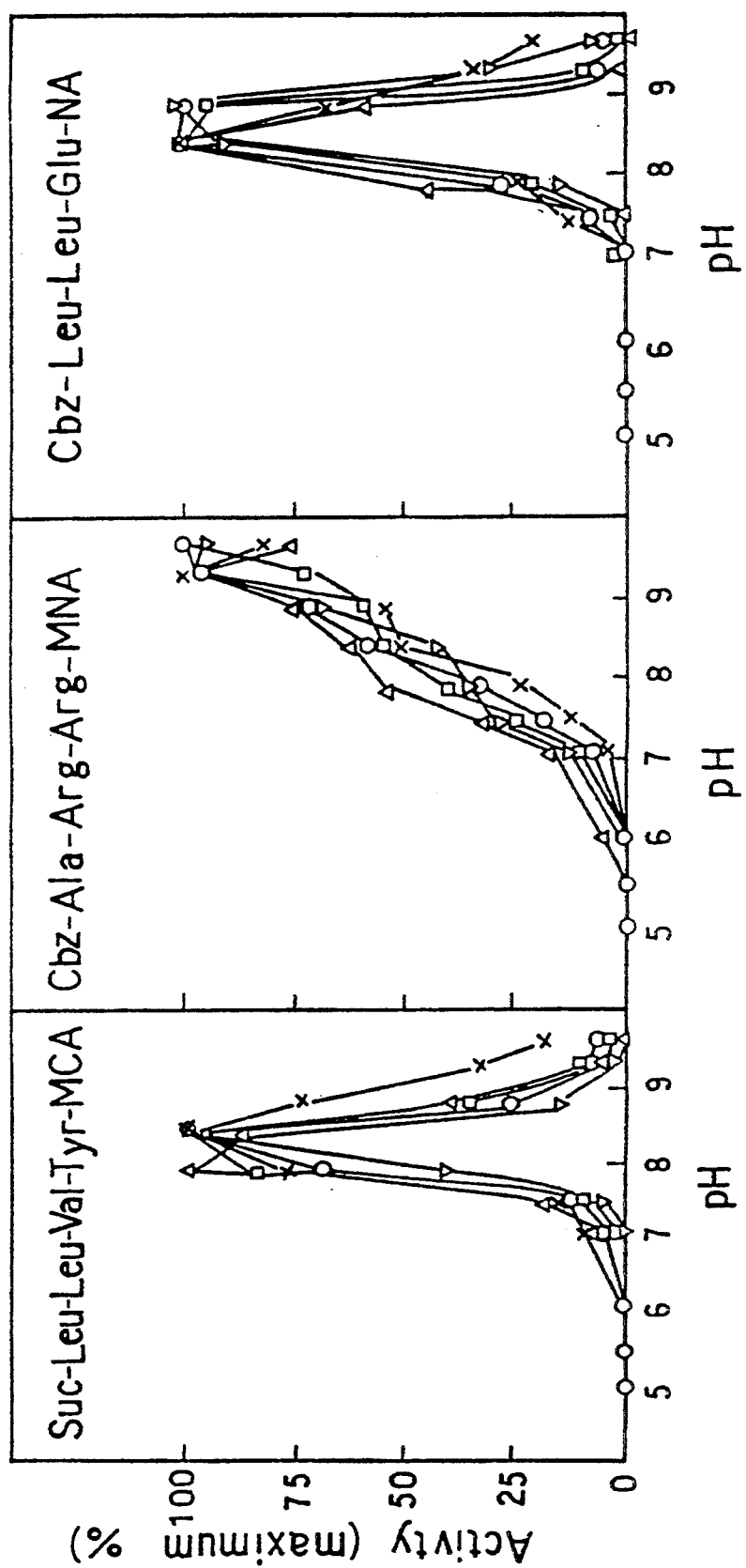
FIG. 1 shows the enzymatic activity of proteasomes of the invention.

The proteasome is present in the inactive form in cells and activated when treated with heat, trypsin, etc.

The present proteasome was tested for activation using poly-L-lysine.

The protease activity was determined in the same manner as above using 5 μg of each proteasome. More specifically, 200 μl of the test solution containing 5 μg of proteasome, 50 mM Tris HCl buffer (pH 8.0), 1 mM dithiothreitol, 10 μg of the substrate and [$^3$H]-casein (25000 cpm) was prepared and thereto added poly-L-lysine (Mw=34000, manufactured by Sigma Chem., Co.) to a final poly-L-lysine concentration of 0.5 mg/ml. The mixture was allowed to react at 37° C. for one hour, and 0.8 ml of 10% trichloroacetic acid containing 2 mg/ml of BSA was added to the reaction mixture to conclude the reaction. The radioactivity of the acid-soluble fraction was determined.

The activity was expressed in decomposition rate (%/h). The result of the test (the test was repeated three times) was given in mean ±S.D.

The result of the decomposition activity (%/h) of [$^3$H]-casein obtained with each of the proteasomes is shown below in Table 1.

TABLE 1

| Test Proteasome | Poly-L-lysine | |
|---|---|---|
| | not added | added |
| Human Proteasome | 1.9 ± 0.3 | 28.4 ± 2.2 |
| Chicken Proteasome | 2.5 ± 0.4 | 18.0 ± 4.0 |
| Xenopus Proteasome | 6.6 ± 0.5 | 34.7 ± 5.9 |
| Yeast Proteasome | 8.2 ± 0.6 | 35.4 ± 5.2 |

(ii) Enzymatic Activity on Synthetic Substrate and Optimal pH

Using as synthetic substrates Suc-Leu-Leu-Val-Tyr-MCA, Cbz-Ala-Arg-Arg-MNA and Cbz-Leu-Leu-Glu-NA, the enzymatic art, and the optimal PH, proteasomes were examined on each of the above substrates according to the method described in the above item (i).

The test was conducted using 0.1M Tris HCl buffer as a buffer and pH was determined directly by means of a pH meter. The proteasome activity (maximum decomposition rate) at varying pH Values was determined according to the above (i). The concentration of the synthetic substrate was 0.2 mM and the reaction time was 10 minutes. To the reaction system were added 100 μl of 10% SDS for conclusion of the reaction and then 2 ml of 0.1M Tris HCl (pH 9.0). MCA, MNA and NA thus released were determined using a fluorophotometer.

The result obtained is shown in FIG. 1.

In FIG. 1, the activity (maximum %) is plotted as the ordinate and the pH as the abscissa. The lines in the figure represent the following:

○—○: Human proteasome
□—□: Rat proteasome
△—△: Chicken proteasome
▽—▽: Xenopus proteasome
×—×: Yeast proteasome The diagram reveals that all of the proteasomes have enzymatic activity against three types of the synthetic substrates which carry in the C-terminal a hydrophobic amino acid which is acidic, basic or neutral. The optimal pH for each of the synthetic substrates was as follows:

[Suc-Leu-Leu-Val-Tyr-MCA]
Human proteasome: pH 8.4–8.6
Chicken proteasome: pH 8.0–8.5
Xenopus proteasome: pH 8.4–8.8
Yeast proteasome: pH 8.4–8.7
[Cbz-Ala-Arg-Arg-MNA]
Human proteasome: pH 9.8–10.1
Chicken proteasome: pH 9.6–10.1
Xenopus proteasome: pH 9.6–10.5
Yeast proteasome: pH 9.6–10.0
[Cbz-Leu-Leu-Glu-NA]
Human proteasome: pH 8.4–8.6
Chicken proteasome: pH 8.4–8.7
Xenopus proteasome: pH 8.9–9.2
Yeast proteasome: pH 8.4–8.8

(iii) Activity Inhibition by Inhibitor

A 2 μg quantity of proteasome was allowed to react with various protease inhibitors at room temperature for one hour. The activity inhibition rate (%) by the inhibitor was determined based on the decomposition rate of the synthetic substrate at the optimal pH. The protease inhibitors tested and their concentrations were as follows:

| | | |
|---|---|---|
| A: Leupeptin | 50 μg/ml |
| B: Chymostatin | 50 μg/ml |
| C: N-ethylmaleimide | 10 mM |
| D: Phenymethanesulfonyl fluoride (PMSF) | 10 mM |
| E: Diisopropyl fluorophosphate (DEP) | 1 mM |
| F: Hemin | 50 μM |

The result obtained using human proteasome is shown below in Table 2.

TABLE 2

| Inhibitor | Inhibition Rate (%) by Inhibitor | | |
|---|---|---|---|
| | Suc—Leu—Leu—Val—Tyr—MCA | Cbz—Ala—Arg—Arg—MNA | Cbz—Leu—Leu—Glu—NA |
| A | 9 | 85 | 0 |
| B | 75 | 19 | 0 |
| C | 88 | 96 | 99 |
| D | 96 | 47 | 99 |
| E | 55 | 15 | 80 |
| F | 40 | 55 | 82 |

The above table reveals that the proteasome has different catalytic sites for different substrates.

Besides the human proteasome, the other proteasomes were tested in the same manner. The result obtained for each of the proteasomes was similar to that shown in Table 2.

<PHYSICAL PROPERTIES>

The physical properties of the proteasome was evaluated.

The sedimentation constant($S_{20,w}$), the diffusion coefficient($D_{20,w}$) the isoelectric point (pI) and the molecular ellipiticity($[\theta]_{220nm}$) for every proteasome were detemined according to the sedimentation velocity method, the quasi-elastic light scattering method, the isoelectric focusing (IEF) method and the circular dichroism method, respectively. These methods are proposed by Tanaka et al. in J. Biol. Chem., 261, 15204–15207 (1986).

The results obtained are shown below in Table 3.

TABLE 3

| Test Proteasome | Sedimentation Constant (S) | Diffusion Coefficient ($cm^2$/s) | pI | Molecular Ellipiticity (deg · $cm^2$/dmol) |
|---|---|---|---|---|
| Human | 21.8 | $2.28 \times 10^{-7}$ | 5.0 | −9800 |
| Chicken | 20.0 | $2.02 \times 10^{-7}$ | 4.9 | −10300 |
| Xenopus | 19.6 | $2.15 \times 10^{-7}$ | 5.0 | −11600 |
| Yeast | 20.0 | $2.60 \times 10^{-7}$ | 4.6 | −9600 |

The molecular weight (M.W.) was calculated from the sedimentation constant and diffusion coefficient shown in Table 3 according to the Svedberg's equation. The Storkes radius (Rh) was calculated from the diffusion coefficient in the same manner. The calculated values and absorption spectrum values (maximum absorption ($\lambda_{max}$) and $E_{1\,cm}^{1\%}$ at 280 nm) are shown in Table 4.

TABLE 4

| Test proteasome | M.W. | Storkes radius | Absorption Spectrum | |
|---|---|---|---|---|
| | | | λmax | $E_{1\,cm}^{1\%}$ (280 nm) |
| Human | 870000 | 94 Å | 278 | 11.2 |
| Chicken | 910000 | 106 Å | 278 | 10.8 |
| Xenopus | 840000 | 98 Å | 278 | 12.3 |
| Yeast | 710000 | 82 Å | 278 | 7.4 |

Neither peaks nor shoulders were observed at 260 nm in the absorption spectrum. It seems that the proteasome of the invention does not carry any nucleic acids.

The contents (mole%) of amino acids in the proteasome were determined under the same condition as in the method of Tanaka et al. (J. Biol. Chem., 261, 15204–15207 (1986)).

The result is shown in Table 5.

TABLE 5

| Amino Acid (mole %) | Proteasome | | | |
|---|---|---|---|---|
| | Human | Chicken | Xenopus | Yeast |
| Asx | 8.4 | 8.2 | 8.7 | 11.0 |
| Glx | 12.4 | 13.1 | 12.5 | 12.9 |
| Arg | 5.5 | 5.4 | 5.2 | 3.6 |
| Lys | 6.2 | 6.0 | 6.7 | 6.2 |
| His | 1.9 | 1.9 | 1.8 | 1.3 |
| Ala | 9.5 | 9.4 | 9.5 | 8.9 |
| Gly | 8.1 | 8.5 | 7.9 | 9.4 |
| Leu | 8.8 | 8.3 | 8.7 | 8.3 |
| Ile | 5.7 | 5.7 | 5.8 | 6.5 |
| Val | 7.2 | 7.0 | 7.1 | 7.1 |
| Phe | 3.4 | 3.3 | 3.4 | 2.8 |
| Tyr | 4.6 | 4.5 | 4.9 | 3.5 |
| Trp | 0.3 | 0.4 | 0.3 | 0.4 |
| Ser | 5.8 | 6.1 | 5.7 | 6.2 |
| Thr | 5.4 | 5.5 | 5.5 | 5.5 |
| ½Cys | N.D. | N.D. | N.D. | N.D. |
| Met | 3.1 | 2.8 | 3.0 | 1.8 |
| Pro | 3.6 | 3.6 | 3.3 | 4.5 |

"N.D." in the above table means "not detected".

<SHAPE OF PROTEASOME>

The human protease was dissolved in a buffer to a concentration of 50 μg/ml. The test solution was added dropwise onto the supporting membrane and then thereonto 1–3% uranyl acetate (pH 4.5) was added to conduct negative staining. The proteasome was then observed with an electron microscope (H7000, manufactured by Hitachi, Ltd., ×50000).

Figure 2:
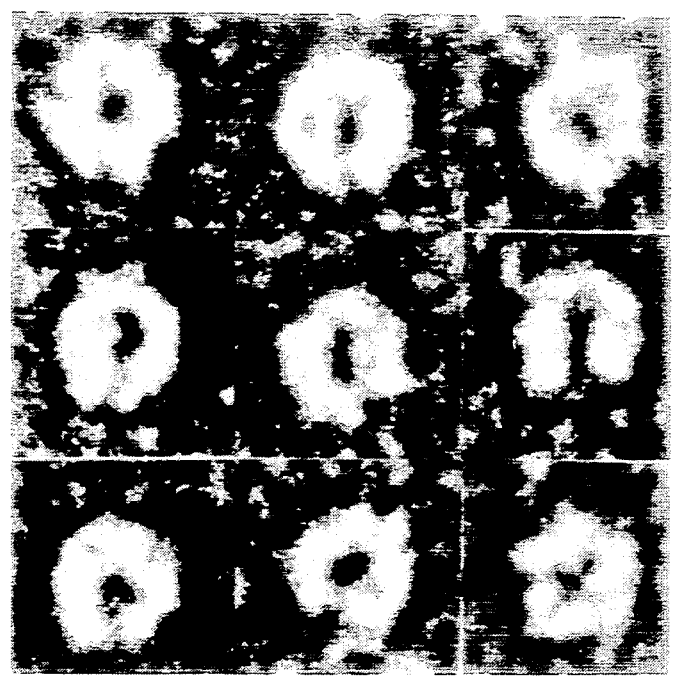
FIG. 2 shows electron micrographs of proteasome molecules negative-stained with uranyl acetate.

The result of microscopic observation of several proteasome molecules is shown in FIG. 2.

FIG. 2 reveals that the human proteasome was observed in the form of a symmetric disk having a cavity in the center. This observation substantially corresponded to the above physical properties.

It was confirmed in the same manner that the other proteasomes, i.e., the chicken proteasome, the Xenopus proteasome and the yeast proteasome are also similarly shaped.

<IMMUNOLOGICAL PROPERTIES OF PROTEASOME>

(i) Reactivity of Polyclonal Antibody

The reactivity of each of the proteasomes with the polyclonal antibodies obtained in Example 3-(1) was evaluated according to Ouchterlony's diffusion method ("Ouchterlony double diffusion analysis", Handbook of Experimental Immunology, Weir, C. ed., pp 655–688, Beckwell Scientific Publications, Oxford) as follows.

A 10 μg portion of the proteasome was placed into a center well on an agar plate, 7 μl portions of the antibodies were placed in side wells on the same plate. Each of the proteasomes was allowed to react with the antibodies in a humidifier at room temperature for 2 days. The plate was washed by being immersed in a phosphate buffer saline (PBS) with, gentle stirring for four days, and then the preciptin arc was protein-stained with Coomassie Brilliant Blue (CBB).

Figure 3:
FIG. 3 and 4 are autoradiograms showing the reactivity of proteasomes of the invention with polyclonal antibodies each prepared from the proteasome.

The result obtained in each proteasome is shown in FIG. 3.

In FIG. 3, the proteasomes placed in the center wells were are as follows:
A: Human protasome (from human liver)
B: Rat proteasome (from rat liver) (J. Biol. Chem., 261, 15197–15203 (1986))
C: Chicken proteasome (from chicken liver)
D: Xenopus proteasome (from *Xenopus laevis* ovary)
E: Yeast proteasome (from *S. cerevisiae*)

The antibodies in the side wells were as follows:
1: Anti-human proteasome antibody
2: Anti-rat proteasome antibody (ibid.)
3: Anti-chicken proteasome antibody
4: Anti-Xenopus proteasome antibody
5: Anti-yeast proteasome antibody
6: Normal rabbit serum FIG. 3 reveals that each of the antibodies obtained in Example 3-(1) exhibited reactivity specific only to the corresponding proteasome, and did not exhibit cross-reactivity with any of the other proteasomes. Therefore, the proteasomes are evidently different from one another.

(ii) Reactivity of Proteasome Subunit

The subunit component of each proteasome was evaluated in immunological reactivity according to immuno blotting analysis as follows.

A 35 μg quantity of each of the proteasome was electrophoresed according to SDS-PAGE (see to <Electrophoresis of Proteasome> described below), then electrically transferred onto Durapore Membrane (product of Japan Milipore Ltd.) using Semi Drug Elactroblotter (product of Sartorius). The membrane was treated with 3% bovine serum and then with 10 μg/ml of the corresponding anti-proteasome antibody (primary antibody). Subsequently the membrane treated was allowed to react with 0.25 μCi/ml of $^{125}$I-protein A as a secondary antibody. The reaction product was analysed by autoradiography.

Figure 4:
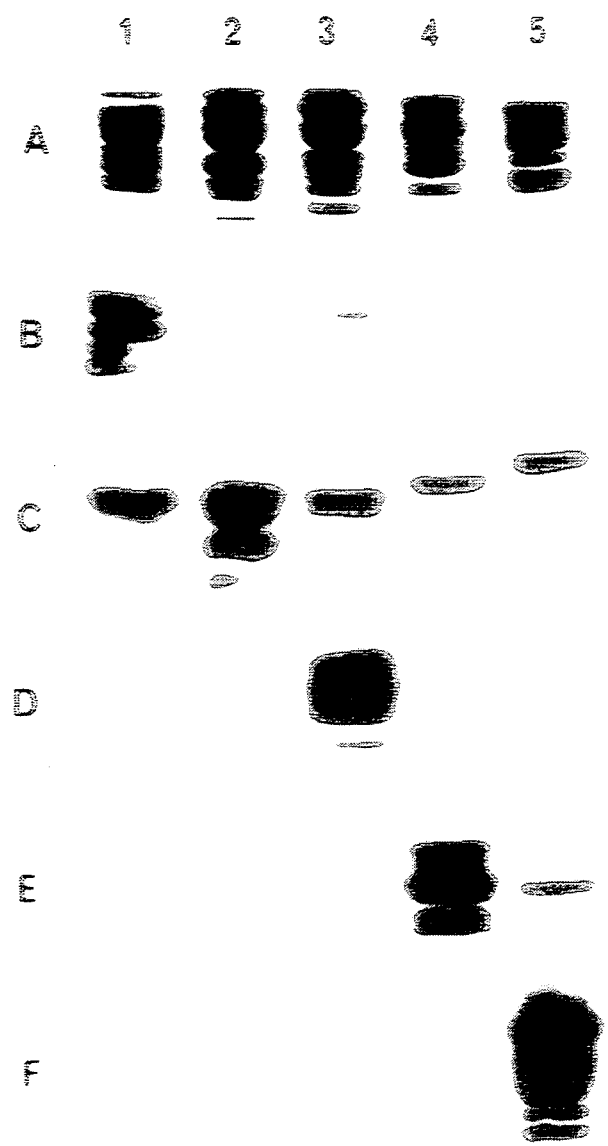

The cross-reactivity for each of the antibodies is shown in FIG. 4 (A to F).

In FIG. 4, A, B, C, D, E and F show the result of protein-staining with CBB in the absence of the primary antibody, the result obtained using the anti-human proteasome antibody, the result obtained using the anti-rat proteasome antibody, the result obtained using the anti-chicken proteasome antibody, the result obtained using the anti-Xenopus proteasome antibody and the result obtained using the anti-yeast proteasome antibody, respectively.

The lanes shows the following specimens:
Lane 1: Human proteasome
Lane 2: Rat proteasome
Lane 3: Chicken proteasome
Lane 4: Xenopus proteasome
Lane 5: Yeast proteasome FIG. 4 reveals that the subunit component of the proteasome was strongly reactive with the polyclonal antibody against the enzyme derived from the same species, but limitedly reactive with the polyclonal antibodies from other species. It was also obverved that some, Subunits are cross-reactive with the antibody from the other species. Therefore, the result shows that the partial structure of the subunit was reatained evolutionarily.

(iii) Reactivity of Monoclonal Antibody

1) Using four kinds of the monoclonal antibodies Nos. 2-17 (No. OAL HMWP-1), 2-21, 2-24 and 4-3 against the human proteasome prepared according to Example 3-(2), the reactivity of the above antibody with the present proteasome was evaluated by ELISA.

More specifically, 50 μl of the monocolonal antibdy and 50 mM phosphate buffer (pH 7.4, containing 0.4% BSA, 0.02% Tween 20 and 0.05% thimerosal) were poured into the immunoplate having 200 μg of the purified human proteasome as immobilized. The plate was incubated with shaking at room temperature for 2 hours, and then washed with three 250 μl portions of deionized water. To the plate was then applied a 100 μl portion of a dilution of enzyme-labeled anti-mouse immunoglobulin (3000-fold dilution of Zymed Hrpo(-product of Zymed Laboratories, Inc.)-labeled goat anti-mouse IgA, IgG and IgM(H,L)). The plate was incubated with stirring at room temperature for 2 hours and washed with three 250 μl portions of deionized water. Thereto was further added 100 μl of a substrate solution, which was prepared by adding 10 μl of 30% $H_2O_2$ to 50 ml of a citrate-phosphate buffer (pH 5.0) containing 0.025% o-phenylene diamine immediately before its use. The plate was allowed to stand at room temperature for 10 minutes and thereto 100 μl of 2N $H_2SO_4$ was added to stop the reaction. The absorbance was determined at 492 nm.

Figure 5:
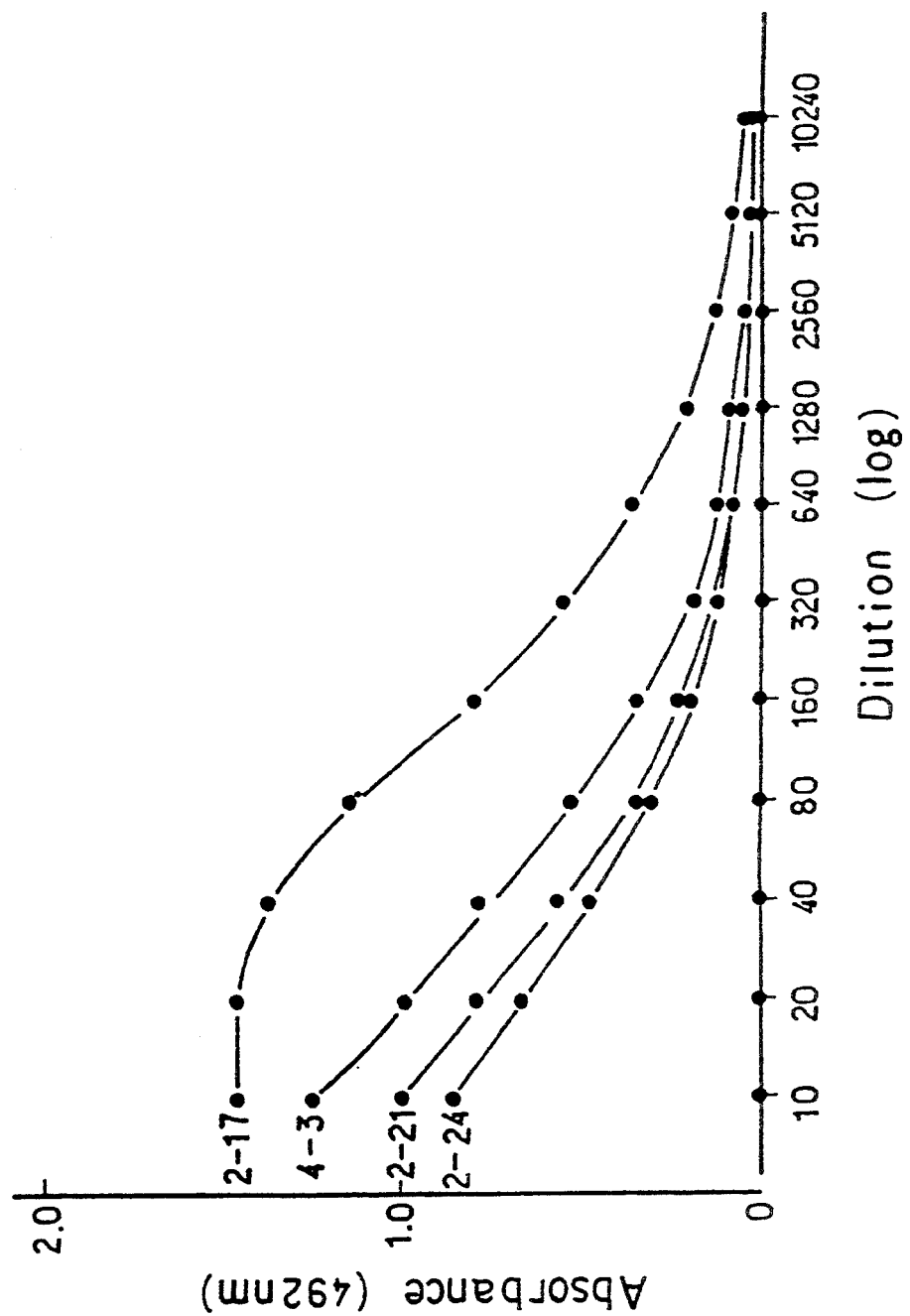
FIG. 5 shows the reactivity of the monoclonal antibody of the invention

The result is shown in FIG. 5. The absorbance (492 nm) is plotted as the ordinate and the dilution as the abscissa.

The monoclonal antibodies in the order of descending reactivity were No. 2-17, No. 4-3, No. 2-21 and No. 2-24.

2) Using the same four kinds of human monoclonal antibodies as used in the above 1), the reactivity of the above antibody with the present proteasome was evaluated in the same manner as the immunoblotting analysis of the polyclonal antibody described in (i), with the exception of using as a primary antibody the medium of the monoclonal antibody-producing hybridoma prepared according to Example 3-(2).

Figure 6:
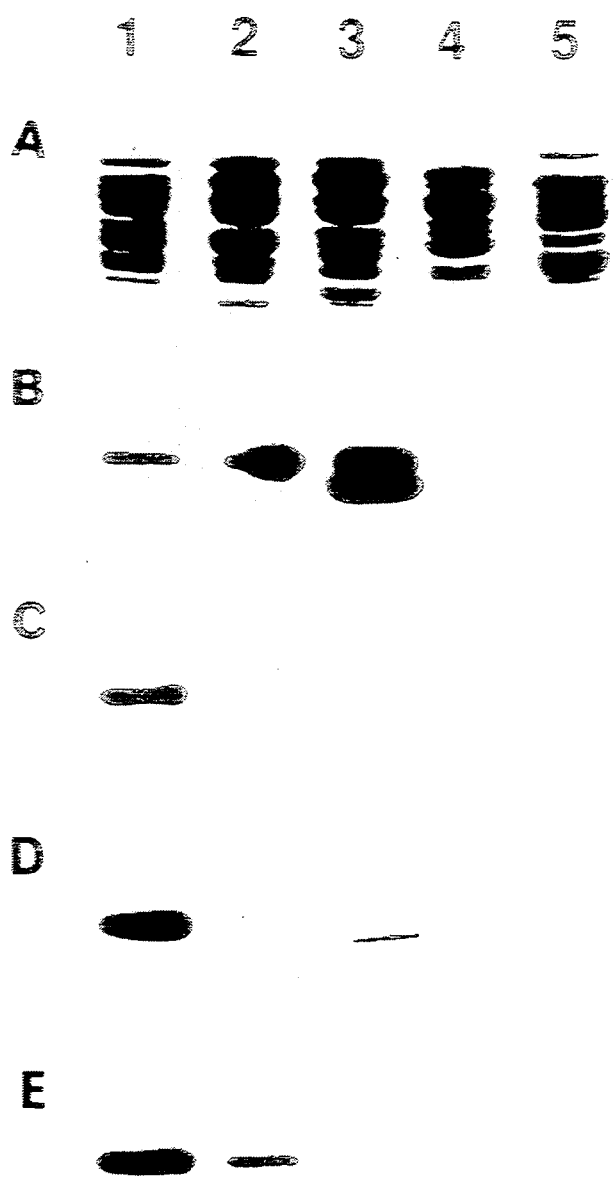
FIG. 6 is an autoradiogram showing the reactivity of proteasomes of the invention with monoclonal antibodies each prepared from the proteasome.

The result of cross-reactivity with each of the antibodies is shown in FIG. 6 in the same manner as in FIG. 4.

In FIG. 6, A, B, C, D and E show the result of protein staining with CBB in the absence of the primary antibody, the result obtained using the human monoclonal antibody No. 2-17, the result obtained using the human monoclonal antibody No. 2-21, the result obtained using the human monoclonal antibody No. 2-24 and the result obtained using the human monoclonal antibody No. 4-3, respectively.

The lanes represent the following specimens:
Lane 1: Human proteasome
Lane 2: Rat proteasome
Lane 3: Chicken proteasome
Lane 4: Xenopus proteasome
Lane 5: Yeast proteasome FIG. 6 reveals that all kinds of the monoclonal anitbodies are strongly reactive with the subunit component having a molecular weight of 30000. The monoclonal antibodies Nos. 2-17 and 4-3 were cross-reactive with the rat proteasome component of the same molecular weight, and the monoclonal antibodies Nos. 2-17 and 2-24 were cross-reactive with the chicken proteasome. This observation clarifies that, although these monoclonal antibodies are reactive with subunits components similar to them, they differ from one another in epitopes. The monoclonal antibodies as such are important as kits useful for immunological identification.

<ELECTROPHORESIS OF PROTEASOME>

The proteasome was electrophoresed on polyacrylamide gel according to Laemmli's method (Nature, 227, pp 680–685 (1970)) in the presence or in the absence of SDS (5% polyacrylamide gel, 35 μg of proteasome)

The result obtained by protein-staining with CBB is shown in FIG. 7. In FIG. 7, the lanes represent the following:

Lane 1: Human proteasome
Lane 2: Rat proteasome
Lane 3: Chicken proteasome
Lane 4: Xenopus proteasome
Lane 5: Yeast proteasome In FIG. 7, each proteasome was electrophoresed as a single band substantiating the homogeneity thereof and the protease activity.

Figure 8:
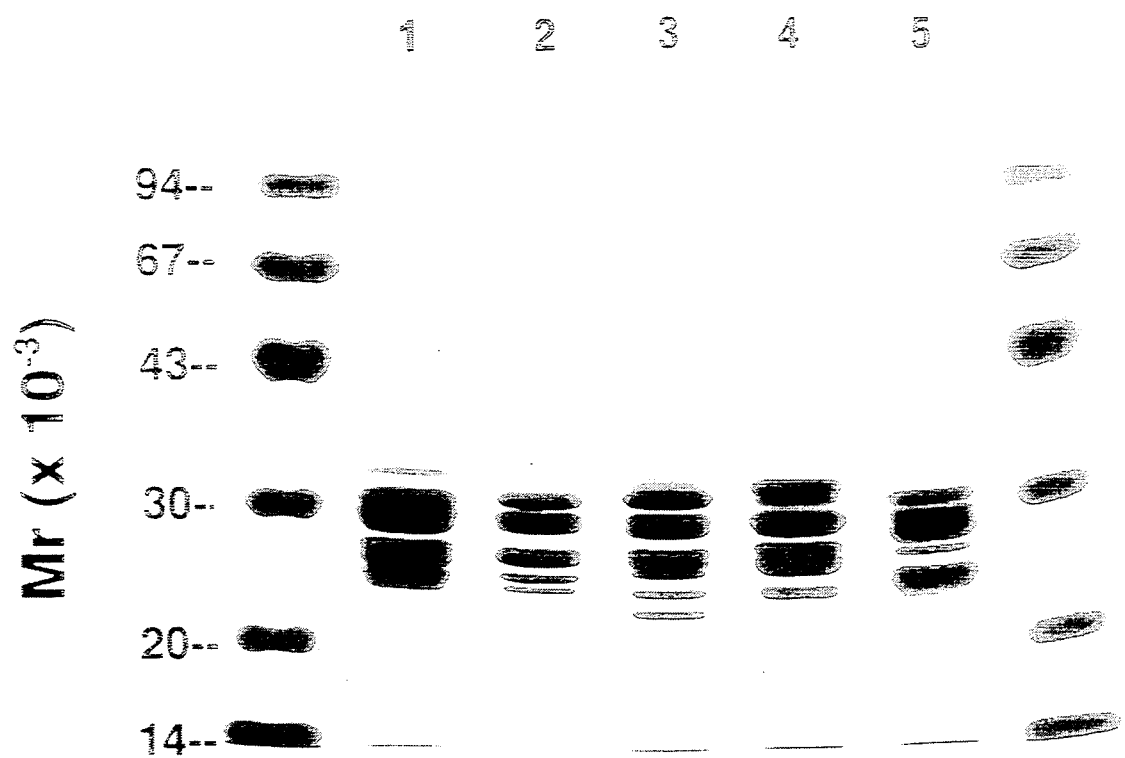

The proteasome was denatured with 1% SDS and then electrophoresed on 15% polyacrylamide gel in the presence of 0.1% SDS. The result is shown in FIG. 8. In FIG. 8, the lanes represent the following:

Lane 1: Human proteasome
Lane 2: Rat proteasome
Lane 3: Chicken proteasome
Lane 4: Xenopus proteasome
Lane 5: Yeast proteasome
Lanes at both ends: Molecular weight marker protein (manufactured by Pharmacia LKB Biotechnology Inc.)

In the diagram, all of the proteasomes are detected as multiple bands ranging in molecular weight from 22000 to 33000. The result shows that the proteasome is a complex (heteropolymer) consisting of many components.

The electrophoresis patterns are similar to one another regardless of the presence of a sulfhydryl reducing agent (2-mercaptoethanol). From this result, it is speculated that no disulfide bond exists in the proteasome.

<ANALYSIS OF PROTEASOME BY CHROMATOGRAPHY>

A 0.5 mg quantity of the proteasome was applied to Cosmosil 5C 4-300 Column (product of Nakarai Chemicals, Ltd.) 10 cm in diameter and 250 cm. in length) equilibrated with 0.5% trifluoroacetic acid (TFA) for reverse phase chromatography under the following conditions:

System: Water Model 141 HPLC System (product of Japan Milipore Ltd.)
Elution: Gradient of acetonitrile containing 0.5% TFA
Flow elution: 1 ml/min
Fraction: 1 ml
Assay: Absorbance (A); at 280 nm (solid line in FIG. 9) and at 215 nm (broken line)

Figure 9:
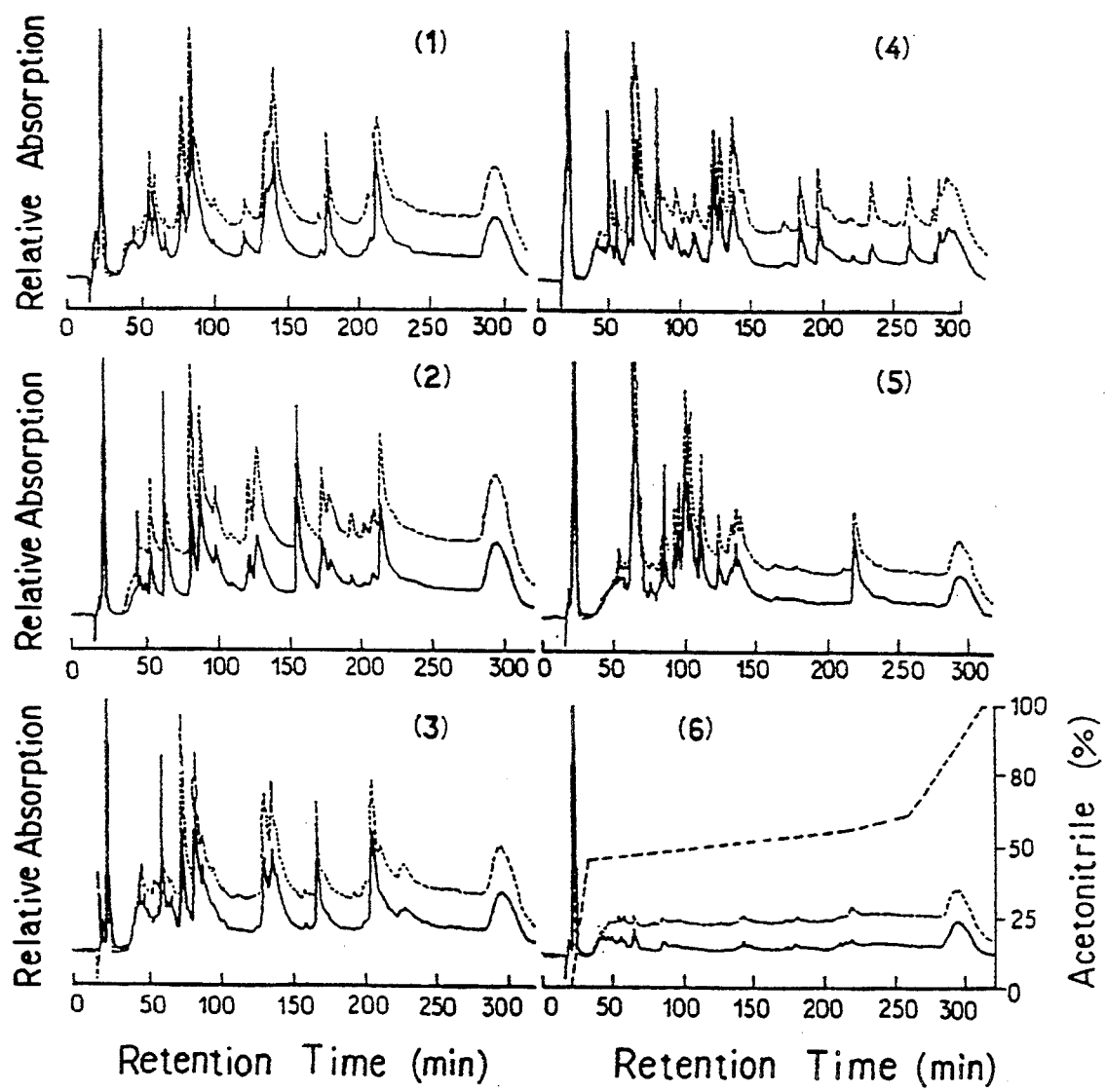
FIG. 9 shows the HPLC elution patterns of proteasomes of the invention.

The result of the elution pattern for each of the proteasomes is shown in FIG. 9. FIGS. 9 (1), (2), (3), (4), (5) and 6) show the results obtained from the human proteasome, the rat proteasome, the chicken proteasome, the Xenopus proteasome, the yeast proteasome and blank, respectively.

The diagram reveals that the proteasomes of the present invention are distinguishable from one another in elution pattern.

<DIAGNOSIS OF CANCERS USING MONOCLONAL ANTIBODY AGAINST PROTEASOME>

(1) Preparation of Plate Having Anti-Human Proteasome Monoclonal Antibody as Immobilized The monoclonal antibody prepared according to Example 3-(2) was adjusted to 5 μg/ml with 50 mM PBS-0.05% $NaN_3$. A 100 μl quantity of the mixture was placed into each of 96 wells of a plate for ELISA (InterMed Nunc-Immuno plate Maxisorp), and the mixture was left to stand overnight at 4° C. to immobilize the monoclonal antibody. Subsequently, the plate was washed with Dulbecco's PBS. A 300 μl quantity of 50 mM pBS-0.05% NaN₃-1% BSA was further palced into each of the wells in order to remove non-specific adsorbate. The plate was then left to stand overnight at 4° C. to immobilize the antibody on the plate.

(2) Diagnosis of Various Diseases by Human Serum

A 100 μl quantity of 50 mM PBS-0.05% NaN₃-0.1% BSA-1.0% glycerol-0.02% Tween 20 (used as an assy buffer) was placed into each of wells of the plate having the antibody as immobilized. With addition of 10 μl of serum specimen, the mixture was incubated with shaking at room temperature for 2 hours.

After incubation, the reaction mixture was washed with Dulbecco's PBS-0.02% Tween 20, and 100 μl of the anti-human proteasome polyclonal antibody (10,000-fold diluted with the assay buffer) was placed into each of the wells, followed by incubation with shaking at room temperature for 2 hours.

The reaction mixture was washed with Dulbecco's PBS-0.02% Tween 20 and 100 μl of a diluent of peroxidase-labeled anti-rabbit immunoglobulin antisera (Zymed HRPO(product of Zymed Laboratories, Inc.)-labeled goat anti-rabbit IgG, IgM) was added to the mixture, followed by incubation with shaking at room temperature for 2 hours. Subsequently the reaction mixture obtained was washed with Dulbecco's PBS-0.02% Tween 20 and into each of the wells was placed 100 μl of a solution of 2.5 mg/ml of o-phenylenediamine in 0.015% H₂O₂ citrate buffer (pH 5.0). The mixture was allowed to stand at room temperature for 10 minutes. Thereto a 100 μl of 2N H₂SO₄ was added to stop the reaction, followed by determination at 492 nm using a microplate reader (manufactured by Titertek Multiskan).

The proportion of positive cases is shown below in the table, the cut-off value being Mean $+2\times$S.D. in healthy adults value.

| Disease | Positive case/Total cases (proportion of positive case %) |
|---|---|
| Benign disease | |
| Hepatitis | 3/8 (37.5%) |
| Cirrhosis | 4/16 (25.0%) |
| Pancreatitis | 0/6 (0%) |
| Nephritis | 1/3 (33.3%) |
| Renal disfunction | 0/7 (0%) |
| Malignant disease | |
| Esophageal cancer | 10/14 (71.4%) |
| Hepatic cancer | 25/40 (62.5%) |
| Pulmonary cancer | 5/6 (83.3%) |
| Ovary cancer | 4/5 (80.0%) |
| Leukemia | 17/37 (45.9%) |

Healthy adults: Mean = 79.5 ng/ml, S.D. = 35.41

The above table shows that the proteasome was detected in patients suffering from malignant diseases in a higher level than in healthy adults. The proteasome is assumed to effuse into blood. Therfore, the detection of the proteasome in serum was considered important in diagnosis of various malignant cancers.

What is claimed is:

1. An isolated and purified yeast polyfunctional protease, wherein the protease has the following enzymological and physicochemical properties:
   a. Enzymatic activity capable of cleaving the synthetic substrate of Cbz-Leu-Leu-Glu-NA at an optimum pH environment of 8.4 to 8.8, wherein Cbz represents N-benzyloxycarbonyl and NA represents 2-naphthylamido;
   b. Enzymatic activity capable of cleaving the synthetic substrate of Cbz-Ala-Arg-Arg-MNA at an optimum pH environment of 9.6 to 100, wherein MNA represents 4-methoxy-2-naphthylamido;
   c. Enzymatic activity capable of cleaving the synthetic substrate of Suc-Leu-Leu-Val-Tyr-MCA at an optimum pH environment of 8.4 to 8.7, wherein Suc represents succinyl and MCA represents 4-methyl-7-cumarylamido;
   d. An ultraviolet absorption spectrum with a maximum absorption ($\lambda$max) at 278 nm and an absorption of $E^{1\%}{}_{1\,cm}=7.4$ at 280 nm;
   e. A sedimentation constant ($S_{20,w}$) of 20.0 S, as determined by the sedimentation velocity method;
   f. A diffusion coefficient ($D_{20,w}$) of $2.60\times10^{-7}$ cm$^2\cdot$S$^{-1}$, as determined by the quasi-elastic light scattering method;
   g. A molecular weight of 710000±50000;
   h. An isoelectric point (pI) of 4.6±0.2, as determined by isoelectric focusing;
   i. The following amino acid composition (mole%):

| Asx | 11.0 | Phe | 2.8 |
|---|---|---|---|
| Glx | 12.9 | Tyr | 3.5 |
| Arg | 3.6 | Trp | 0.4 |
| Lys | 6.2 | Ser | 6.2 |
| His | 1.3 | Thr | 5.5 |
| Ala | 8.9 | ½ Cys | ND |
| Gly | 9.4 | Met | 1.8 |
| Leu | 8.3 | Pro | 4.5 |
| Ile | 6.5 | Val | 7.1 | wherein ND means that the amino acid is not detectable.

* * * * *